United States Patent [19]
Gibilisco

[11] Patent Number: 5,207,657
[45] Date of Patent: May 4, 1993

[54] RECESSED TIP FLUID DISPENSER

[75] Inventor: Kenneth J. Gibilisco, Coopersburg, Pa.

[73] Assignee: Merck & Co., Inc., Rahway, N.J.

[21] Appl. No.: 761,554

[22] Filed: Sep. 18, 1991

[51] Int. Cl.$^5$ .................... A61M 35/00; B65D 55/02; B65D 51/18; B67D 5/06
[52] U.S. Cl. .................... 604/295; 604/294; 604/310; 222/182; 222/420; 222/546; 222/556; 220/256; 220/335; 220/339; 215/216; 215/225; 215/306
[58] Field of Search .............. 604/294, 295, 298, 310; 222/546, 556, 550, 182, 420; 215/306, 216, 225; 220/256, 335, 339

[56] References Cited

U.S. PATENT DOCUMENTS

| 2,330,939 | 10/1943 | Wilson | 215/307 |
| 3,945,381 | 3/1976 | Silver . | |
| 4,111,200 | 9/1978 | Sbarra et al. . | |
| 4,500,016 | 2/1985 | Funfstuck | 222/557 |
| 4,733,802 | 3/1988 | Sheldon | 222/181 |
| 4,834,728 | 5/1989 | McKenna | 604/301 |
| 4,915,268 | 4/1990 | Lay et al. | 222/556 |

OTHER PUBLICATIONS

Hording et al., Acta Opthalmologica, 60: 213-222 (1982).

Primary Examiner—Randall L. Green
Assistant Examiner—Paul Zuttarelli

[57] ABSTRACT

A dispenser for liquids, e.g., ophthalmic liquids, is provided with a movable top that pivots open to expose a recessed dispensing tip and pivots closed to cover and seal the dispensing tip.

16 Claims, 2 Drawing Sheets

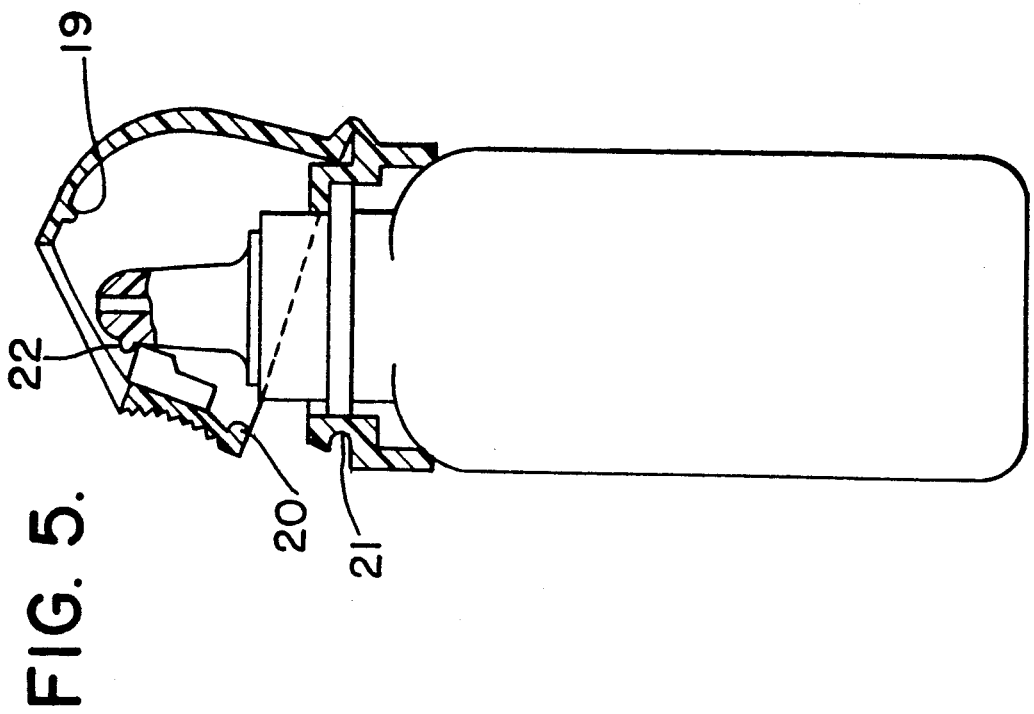
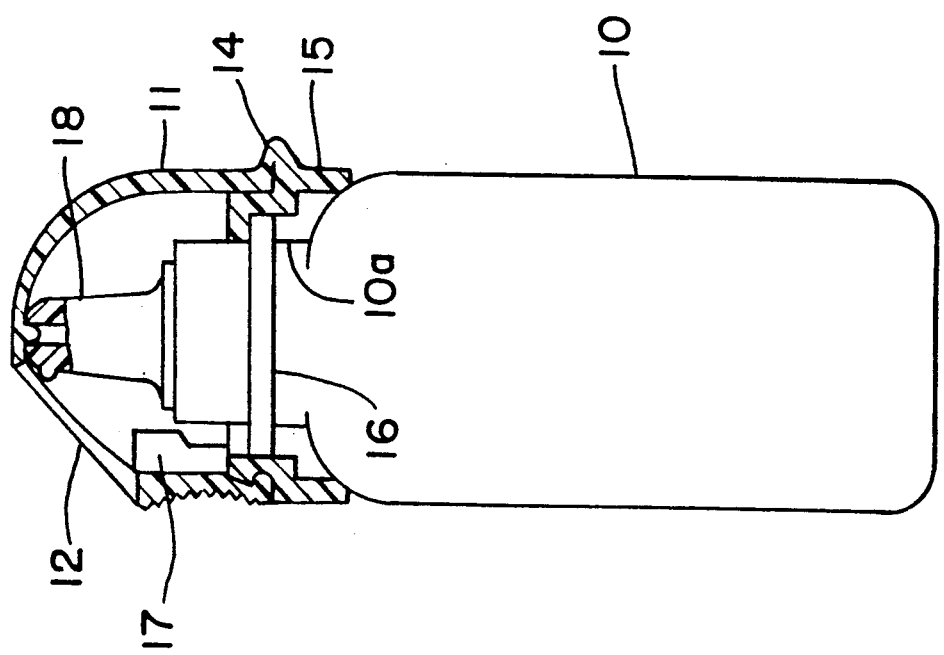

5,207,657

RECESSED TIP FLUID DISPENSER

BACKGROUND OF THE INVENTION

A significant problem with previous devices for dispensing opthalmic solutions is contamination of the dropper nozzle by inadvertent contact with the eye and other surfaces. The problem is described by Hovding et al., Acta Opthalmologica, 60: 213-222 (1982). This contact also can clog the orifice of the tip, making it impossible to dispense further drops. Contamination of the nozzle can then result in microbial contamination of the solution remaining in the dropper bottle and the transfer of this contamination to either or both eyes.

One common route of this contamination comprises touching the dropper nozzle to the surface of the eye during administration of medication. The contact permits contamination of the fluid remaining in the nozzle, which liquid ultimately flows back into the dropper bottle, contaminating the entire contents, and sometimes eventually plugging the dispenser tip.

Some devices have been reported which serve to prevent contact of a dropper nozzle but which were designed primarily to aid in aiming the dropper nozzle properly. See for example U.S. Pat. Nos. 4,834,728; 3,945,381; 4,111,200 and 4,733,802. These devices generally comprise a large cup-shaped or cone-shaped member, the rim of which rests on the patient's face over the eye socket and have a tip composed of a nozzle protruding through the cup-shaped member oriented so that drops from the nozzle will enter the eye.

These reported devices are fairly large, cumbersome and not easily carried in a handbag or pocket. The diameter of the cup-shaped member is large enough to permit easy contact of the dropper tip with fingers or other septic objects resulting in contamination of the device and its contents. Furthermore, covering of the eye with the large cup-shaped member may actually increase the blink reflex, thus raising the likelihood that the drop will miss the intended target.

OBJECTS OF THE INVENTION

It is an object of the present invention to provide a fluid dispensing device having a movable top that opens to expose a recessed dispensing tip and that closes to cover and seal the dispensing tip. A further object is to provide a fluid dispensing device having a top with restricted movement that locks in both open and closed positions. Another object is to provide a fluid dispensing device that prevents contamination of the fluid contents during dispensing. Still another object is to provide a fluid dispensing device that may be easily opened and closed by patients having limited or impaired manual dexterity. Yet another object is to provide a fluid dispensing device whose top cannot be dropped or lost. These and other objects of the present invention will be apparent from the following description.

SUMMARY OF THE INVENTION

A two-piece dispenser for a sterile liquid has a body and a movable top that covers and seals the dispensing means when locked in close position and which pivots and locks in open position to expose a recessed dispensing tip.

BRIEF DESCRIPTION OF THE DRAWINGS

FIG. 4 is a cross-sectional view taken along the line 1—1 of FIG. 1, FIG. 5 is a side elevation partly in cross-section showing the cap in open position.

Figure 1:
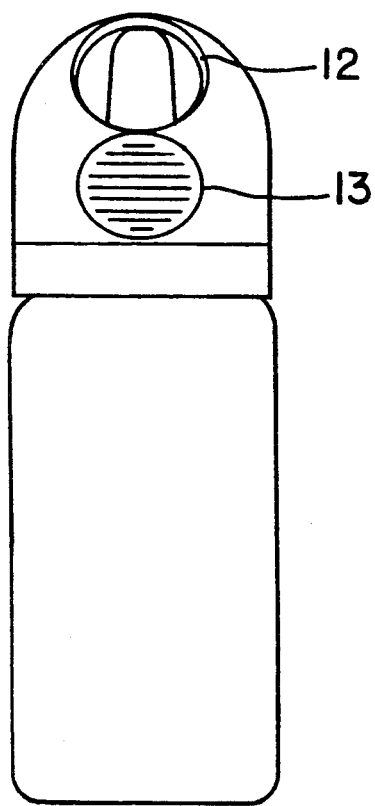
FIG. 1 is a front elevation of the recessed tip fluid dispenser of the present invention.
Figure 2:
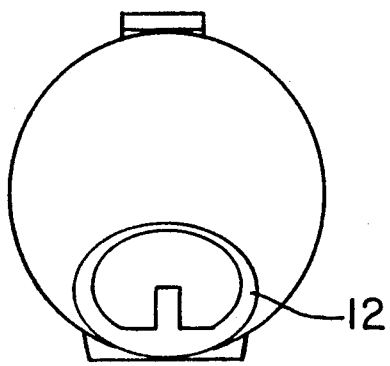
FIG. 2 is a plan view.
Figure 3:
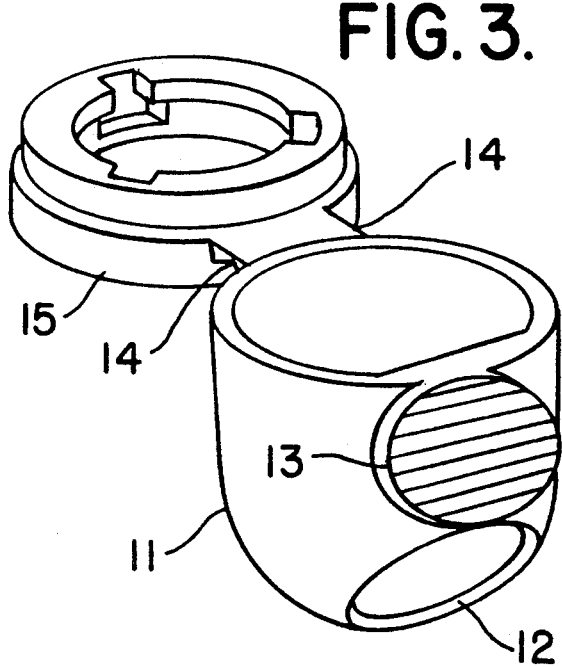
FIG. 3 is a perspective view of the pivoting top.

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION

The fluid dispensing device of the present invention is intended for delivery of sterile fluids such as ophthalmic fluids intended for administration to the eye, or sterile fluids intended for administration to any bodily surface. The fluid dispensing device of the present invention has recessed dispensing means so that fluids can be dispensed without the dispensing means contacting the surface to which the fluids are administered.

The fluid dispensing means of the present invention consists of a bottle 10 which can be formed from a variety of materials such as, for example, soft or hard plastic, e.g., polypropylene or low density polyethylene, or other manually deformable material, or glass. The bottle, if made of plastic, can be produced by conventional blow molding technique. It is to be understood that the bottle of the present invention is not limited to any specific material or to its manufacture by any specific process as it will be understood by those skilled in the art that many different materials and various manufacturing techniques can be employed.

Bottle 10 is adapted to contain a liquid medication, preferably a physiologically acceptable, liquid ophthalmic medication. The upper portion of the bottle 10 has neck 10a that is tapered to provide a dispenser tip 18. The bottle 10 is fitted with a cap 11 provided with an aperture 12 in its upper sidewall and with thumb rest 13. Aperture 12 covers dispensing tip 18 when cap 11 is closed but exposes tip 18 when cap 11 is opened. Tip 18 is always maintained below the plane of aperture 12 when cap 11 is in opened position. Tip 18 has an internal channel communicating with the bottle (not shown as obvious) and is calibrated to deliver a predetermined amount of liquid.

The cap 11 is pivotably attached by hinge means 14 to ring 15 that fits over transfer bead 16 on the neck 10a of bottle 10. The hinge can be a living hinge as shown or a true hinge in the case of a two-piece cap.

The interior upper surface of cap 11 is provided with closure means 19 adapted to fit into and seal the opening of dispenser tip 18, thereby preventing foreign matter from entering and contaminating the contents of the bottle, and/or plugging the dispenser tip.

The cap is provided with means that cooperate with means on the bottle and the dispensing tip to lock the cap in closed and open positions, respectively. Thus, the inner wall of cap 11 is provided with bead 20 which fits into indent 21 on ring 15 to lock cap 11 in its closed position. Bead 22 on dispenser tip 18 engages the top of inner flange 17 to lock cap 11 in its open position. Whether cap 11 is fully or partly opened, tip 18 is always below the plane of aperture 12 whereby the tip 18 is protected from contamination during dispensing of contents of the bottle. As it will be obvious that other locking means can be employed, it is to be understood that the present invention is not limited to the specific locking means described above.

What is claimed is:

1. A container for storing and dispensing a liquid comprising a body having a neck and a liquid dispensing tip having an opening, a cap having an upper sidewall and an interior surface, fastened to the body and said cup being pivotable away from the body, the cap having an aperture in its upper sidewall through which liquid is dispensed, the apertures in the cap exposing the dispensing tip in both open and closed positions, the cap being pivoted away from the body thereby aligning the aperture of the cap with the opening of the dispensing tip when the container is in the open position, the cap being pivoted toward the body, thereby moving the aperature of the cap out of alignment with the opening of the dispensing tip to close the container.

2. A container according to claim 1 wherein the cap is provided with means to contact and seal the dispensing tip when the cap is in the closed position.

3. A container according to claim 2 wherein the means is located on the interior surface of the cap.

4. A container according to claim 3 wherein the means comprises a bead.

5. A container according to claim 1 wherein a transfer bead surrounds the neck.

6. A container according to claim 5 wherein a ring is attached to the transfer bead.

7. A container according to claim 6 wherein the cap is attached to the ring that is fitted over the transfer bead.

8. A container according to claim 7 wherein the cap is attached to the ring by a hinge means.

9. A container according to claim 8 wherein the hinge is a living hinge.

10. A container according to claim 7 having a thumb rest.

11. A container according to claim 7 wherein the container is provided with means to lock the cap in the closed position.

12. A container according to claim 11 wherein the means comprise complementary means on the cap and the ring.

13. A container according to claim 12 wherein the means comprise a bead and an indent.

14. A container according to claim 7 wherein the container is provided with means to lock the cap in the open position.

15. A container according to claim 14 wherein the means comprise complementary means on the cap and the dispensing tip.

16. A container according to claim 15 wherein the means comprise a bead and a flange.

* * * * *